United States Patent [19]

Choi et al.

[11] Patent Number: 5,698,588

[45] Date of Patent: Dec. 16, 1997

[54] HALOGEN SUBSTITUTED CARBAMATE COMPOUNDS FROM 2-PHENYL-1,2-ETHANEDIOL

[75] Inventors: Yong Moon Choi, Towaco; Min Woo Kim, Montville, both of N.J.

[73] Assignee: Yukong Limited, Seoul, Rep. of Korea

[21] Appl. No.: 586,497

[22] Filed: Jan. 16, 1996

[51] Int. Cl.$^6$ .................................................. A61K 31/27
[52] U.S. Cl. ..................... 514/483; 560/164; 514/489
[58] Field of Search ........................ 560/164; 514/483, 514/489

[56] References Cited

U.S. PATENT DOCUMENTS

| | | | |
|---|---|---|---|
| 2,884,444 | 4/1959 | Berger | 260/482 |
| 2,937,119 | 5/1960 | Berger et al. | 167/68 |
| 3,144,389 | 8/1964 | Bossinger | 560/164 |
| 3,248,418 | 4/1966 | Bossinger | 560/164 |
| 3,265,727 | 8/1966 | Bossinger | 560/164 |
| 3,265,728 | 8/1966 | Bossing et al. | 260/482 |
| 3,313,692 | 4/1967 | Bossinger | 560/124 |
| 3,313,696 | 4/1967 | Bossinger | 560/164 |
| 3,313,697 | 4/1967 | Bossinger | 560/164 |
| 3,313,699 | 4/1967 | Bossinger | 560/164 |
| 3,313,700 | 4/1967 | Bossinger | 560/164 |
| 3,509,162 | 4/1970 | Bsendorfetal | 260/294 |

OTHER PUBLICATIONS

Bergen, "J. Pharm. Exp. Ther." 104, 229–233 (1952).
DeSala et al. "Toxicology and Applied Pharmacology", 2, 397–402 (1960).

*Primary Examiner*—Michael L. Shippen
*Attorney, Agent, or Firm*—Abelman, Frayne & Schwab

[57] ABSTRACT

The pure enantiomeric forms, as well as enantiomeric mixtures excluding the racemic mixture of monocarbamates of 2-phenyl-1,2-ethanediol substituted with more than one halogen atom on the phenyl ring and dicarbamates of 2-phenyl-1,2-ethanediol substituted with more than one halogen atom on the phenyl ring have been found to be effective in the treatment of disorders of the central nervous system.

7 Claims, No Drawings

HALOGEN SUBSTITUTED CARBAMATE COMPOUNDS FROM 2-PHENYL-1,2-ETHANEDIOL

FIELD OF THE INVENTION

The present invention relates to novel pharmaceutically useful organic compounds. These compounds are the pure enantiomeric forms, as well as the mixtures in any ratio of the two enantiomers of 2-phenyl-1,2-ethanediol carbamate compounds with at least one halogen substituent on the phenyl ring represented by the formulas (I), (II) and (III), wherein X may be at least one halogen atom substituted on the phenyl ring, excluding the racemic mixture of the compounds represented by the structural formulas (I) and (II). More particularly, the aforementioned compounds have been found to be effective in the treatment of central nervous system disorders, especially as anticonvulsants, neuroprotective agents and muscle relaxants.

Formulas

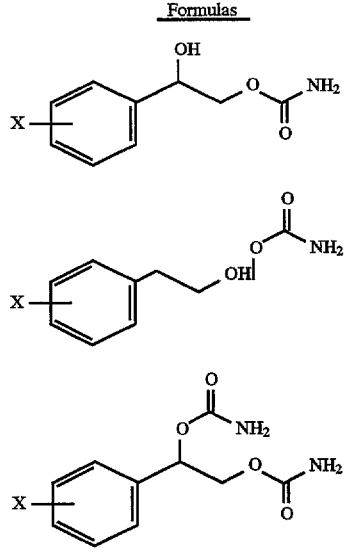

DESCRIPTION OF THE PRIOR ART

Carbamate compounds of aryl alkyl alcohols have been known to be useful as antiepileptics and as muscle relaxants. It was reported in Toxicol. And Appl. Pharm. 2, 397–402 (1960) that when X is hydrogen in structural formula (I), the compounds is effective as an antiepileptic. Dicarbamate compounds of 2-methyl-3-propyl-1,3-propanediol has been reported and their pharmacological effects have been described in J. Pharmacol. Exp. Ther., 104, 229 (1952).

In U.S. Pat. No. 3,265,728, carbamate compounds represented by the structural formula (IV) with a substituent on the phenyl ring has been disclosed as useful in treating central nervous system disorders. In the structural formula (IV), $R_1$ is carbamate or methylene carbamate, $R_2$ is alkyl with 1–2 carbons, hydroxyalkyl with 1–2 carbons, hydroxy or hydrogen, $R_3$ is hydrogen, alkyl with 1–2 carbons and X is halogen atom comprising of fluorine, chlorine, bromine and iodine, methyl, methoxy, phenyl, nitro or amine group.

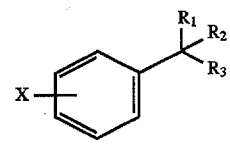

In U.S. Pat. No. 2,884,444, dicarbamate compounds from 2-phenyl-1,3-propanediol have been disclosed, and in U.S. Pat. No. 2,937,119 carbamate compounds such as isopropylmeprobamate have been disclosed.

The carbamate compounds described in the previous paragraph are currently being used in the treatment of central nervous system disorders, although efforts are being made to find new carbamate compounds for use in the treatment of various central nervous system diseases.

It is an object of the present invention to provide novel carbamate compounds for therapeutic use, especially compositions containing such carbamate compounds as the active ingredient, which possess therapeutic activity in treating diseases of the central nervous system.

SUMMARY OF THE INVENTION

In order to achieve the foregoing object, as well as other objects of the present invention, the carbamate compounds represented by the structural formulas (I), (II) and (III) have a chiral carbon on its benzylic position, hence there can be two optical enantiomers of the compounds represented by the structural formulas (I), (II) and (III). Generally speaking, optical enantiomers of various compounds exhibit different pharmacological and toxicological activities, and it is the current trend in the pharmaceutical industry to develop one enantiomer with either fewer toxicological effects or better efficacy.

This invention discloses the pure enantiomeric forms, as well as the mixtures in any ratio of the two enantiomers of 2-phenyl-1,2-ethanediol carbamate compounds with at least one halogen substituent on the phenyl ring represented by the formulas (I), (II) and (III), wherein X may be at least one halogen atom substituted at any positions on the phenyl ring including the ortho meta or para positions, excluding the racemic mixture of the compounds represented by the structural formulas (I) and (II), which are useful in the treatment of central nervous system diseases, particularly as antiepileptics, neuroprotective agents and centrally acting muscle relaxants.

DETAILED DESCRIPTION OF THE INVENTION

This invention provides novel pharmaceutically useful organic carbamate compounds represented by the structural formulas (I), (II) and (III), wherein X may be at least one halogen atom substituted at any positions on the phenyl ring including the ortho, meta or para positions.

Formulas

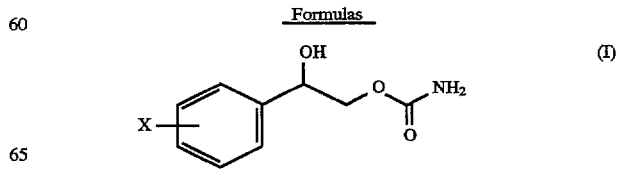

-continued
Formulas

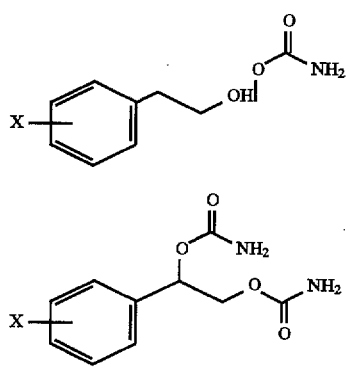

The compounds of this invention possess selective pharmacological properties and are useful in treating and preventing central nervous system disorders including epilepsy, stroke and muscle spasm.

It will be apparent to those skilled in the art that the compounds of the present invention contain chiral centers. The compounds of formula (I), (II) and (III) contain an asymmetric carbon atom at the benzylic position, which is the aliphatic carbon adjacent to the phenyl ring. The therapeutic properties of the compounds may to a greater or lesser degree depend on the stereochemistry of a particular compound. The scope of the present invention includes all enantiomeric forms of formulas (I), (II) and (III), either in their pure form or as mixtures of enantiomers. Pure enantiomers as well as enantiomeric mixtures are within the scope of the present invention.

The carbamates compounds represented by the structural formulas (I) and (II) may be prepared by the synthetic method described in Scheme 1, a detailed description of which follows. A 2-phenyl-1,2-ethanediol with a halogen substituent on the phenyl ring is reacted with dimethyl carbonate in the presence of catalytic amount of sodium methoxide and the by-product methanol is removed by a vacuum distillation and the residual product is dried in vacuo. The crude reaction product is subsequently dissolved in a lower alkanol, such as methanol, and excess ammonium hydroxide (28–30%) is added to the reaction solution at room temperature to provide two regioisomeric forms of a monocarbamate of 2-phenyl-1,2-ethanediol with a halogen substituent on the phenyl ring. Regioisomeric forms of monocarbamates of 2-phenyl-1,2-ethanediol with a halogen substituent on the phenyl ring are separated by flash column chromatography.

In the structural formulas (I) and (II) in Scheme 1, X may be fluorine, chlorine, bromine or iodine atoms substituted at the ortho, meta or para positions of the phenyl ring.

The carbamate compounds represented by the structural formula (III) may be prepared by the synthetic method described in Scheme 2, and a detailed description of which follows. A 2-phenyl-1,2-ethanediol with a halogen substituent on the phenyl ring is dissolved in dichloromethane and is treated with 10 equivalents of sodium cyanate and 10 equivalents of methanesulfonic acid. The reaction mixture is stirred until the reaction is complete as evidenced by thin layer chromatography, and the mixture is washed with aqueous base solution, extracted with dichloromethane and the desired product is purified by flash column chromatography.

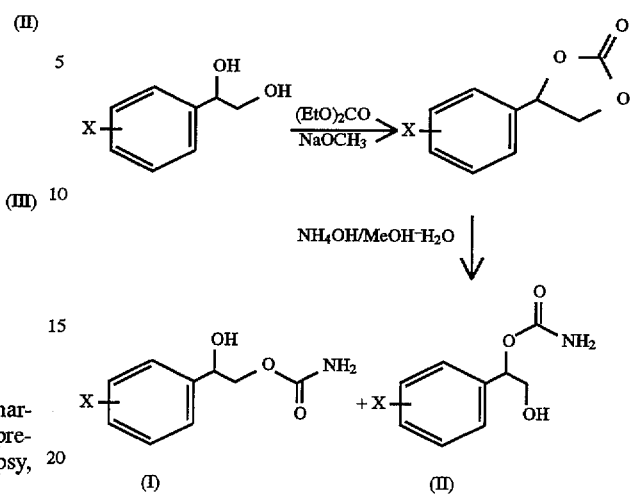

In the structural formulas (I) and (II) in Scheme 2, X may be a fluorine, chlorine, bromine or iodine atoms substituted at the ortho, meta or para positions of the phenyl ring.

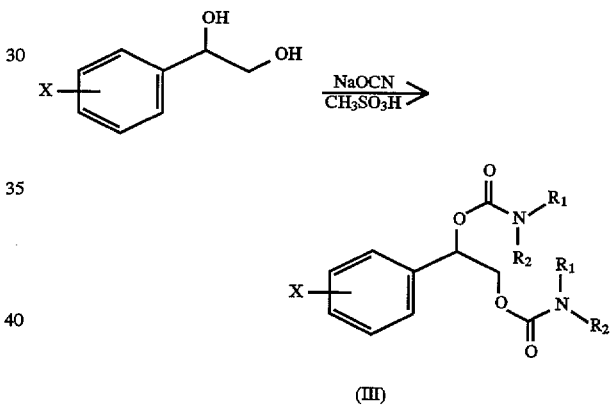

In utilizing the compounds of the present invention for the treatment of diseases of the central nervous system, particularly the treatment of epilepsy, stroke and muscle spasm, it is preferred to administer the compounds orally. Since the compounds are well absorbed orally, it usually will not be necessary to resort to parenteral administration. For oral administration, the present carbamate compounds are preferably combined with a pharmaceutical carrier. The ratio of the carrier to the compounds of the present invention is not critical to achieve the effects of the medicine on the central nervous system, and they can vary considerably, depending on whether the composition is to be filled into capsules or formed into tablets. In tableting, it is usually desirable to employ at least as much pharmaceutical carrier as the pharmaceutically active ingredients. Various edible pharmaceutical carriers or mixtures thereof can be used. Suitable carriers, for example, are a mixture of lactose, dibasic calcium phosphate and corn starch. Other pharmaceutically acceptable ingredients can be farther added, including lubricants such as magnesium stearate.

A better under standing of the present invention may be obtained in light of following examples which are set forth to illustrate, but are not to be construed to limit, the present invention.

EXAMPLE 1

(D/L)-1-m-Chlorophenyl-1,2-ethanediol

In a 2 L 3 neck round bottom flask equipped with a mechanical stirrer, potassium osmate (52 mg), potassium ferricyanide (69.2 g), and potassium carbonate (29.02 g) were dissolved in t-butanol (300 mL) and deionized water (300 mL), and the mixture was cooled in an ice bath. To the reaction mixture m-chlorostyrene (9.74 g) was added and the reaction mixture was stirred for 18 hours at room temperature. After extracting with dichloromethane (200 mL), the combined organic phase was dried over anhydrous sodium sulfate, filtered and concentrated. (D/L)-1-m-Chlorophenyl-1,2-ethanediol (10.8 g, yield 90%) was purified by a flash column chromatography.

EXAMPLE 2

(D/L)-1-m-Chlorophenyl-1,2-ethanediol carbonate

In a 50 mL round bottom flask equipped with vacuum distillation apparatus, 1-phenyl-1,2-ethanediol (9.74 g), diethyl carbonate (10.25 mL) and sodium methoxide (305 mg) were placed and the resulting mixture was heated in an oil bath up to 135° C. with magnetic stirring. The by-product, ethyl alcohol was collected in a receiver flask. After collecting approximately 10 mL of ethanol, the residual ethyl alcohol remaining in the reaction mixture was removed by vacuum distillation. The reaction mixture was cooled to room temperature, dissolved in dichloromethane (40 mL), washed with brine (15 mL), dried over anhydrous sodium sulfate, filtered and then concentrated in vacuo to produce (D/L)-1-m-Chlorophenyl-1,2-ethanediol carbonate (11.05 g, yield 99%).

EXAMPLE 3

(D/L)-2-carbamoyloxy-1-m-chlorophenylethanol

In a 250 mL round bottom flask equipped with a magnetic stirrer, (D/L)-1-m-Chlorophenyl-1,2-ethanediol carbonate (10.95 g) was dissolved in methanol (60 mL) and the mixture was cooled in an ice bath. Ammonium hydroxide (30 mL, 28–30%) was added to the mixture and the mixture was stirred at room temperature for 1 hour or until the reaction was completed as evidenced by thin layer chromatography. Excess ammonium hydroxide and methanol were removed in vacuo to yield a white solid. (D/L)-2-Carbamoyloxy-1-m-chlorophenylethanol (1.25 g, yield 10%, m.p. 90° C.) was purified by flash column chromatography.

EXAMPLE 4

(D/L)-1-o-Chlorophenyl-1,2-ethanediol (D/L)-1-o-Chlorophenyl-1,2-ethanediol (11.5 g, yield 90%, m.p. 109° C.) was prepared using the same synthetic method described in Example 1, except that o-chlorostyrene (10.21 g) was used instead of m-chlorostyrene

EXAMPLE 5

(D/L)-1-o-Chlorophenyl-1,2-ethanediol carbonate (D/L)-1-o-Chlorophenyl-1,2-ethanediol carbonate (12.58 g, yield 100%) was prepared using the same synthetic method described in Example 2, except that (D/L)-o-chlorophenyl-1,2-ethanediol (10.98 g) was used instead of (D/L)-1-m-chlorophenyl-1,2-ethanediol.

EXAMPLE 6

(D/L)-2-carbamoyloxy-1-o-chlorophenylethanol and
(D/L)-2-carbamoyloxy-2-o-chlorophenylethanol In a 200 mL round bottom flask equipped with a magnetic stirrer, approximately 12 mL of liquid ammonia was condensed at −78° C., and (D/L)-1-o-Chlorophenyl-1,2-ethanediol carbonate (6.0 g) in methanol (200 mL) was added slowly. The reaction mixture was slowly warmed to room temperature and was stirred at room temperature for another hour, and then concentrated in vacuo. (D/L)-2-Carbamoyloxy-1-o-chlorophenylethanol (1.97 g, yield 30%, m.p. 100° C.) and (D/L)-2-carbamoyloxy-2-o-chorophenylethanol (1.77 g) with minor impurities was obtained after a chromatographic purification. The impure (D/L)-2-carbamoyloxy-2-o-chorophenylethanol was treated in hot acetone and the resulting mixture was cooled to room temperature and filtered to yield analytically pure (D/L)-2-carbamoyloxy-2-o-chorophenylethanol (1.15 g, 18%, m.p. 183° C.).

EXAMPLE 7

(D/L)-2-Carbamoyloxy-2-o-chlorophenylethyl carbamate (D/L)-1-o-Chlorophenyl-1,2-ethanediol was dissolved in tetrahydrofuran (115 mL) and sodium cyanate (9.0 g) and methanesulfonic acid (9.5 mL) was added in an ice bath. The resulting reaction mixture was stirred for 18 hours, extracted with tetrahydrofuran-dichloromethane mixture, washed with 5% aqueous sodium hydroxide, dried over sodium sulfate, filtered, concentrated and purified by flash column chromatography to yield a white solid. Analytically pure (D/L)-2-Carbamoyloxy-2-o-chlorophenylethyl carbamate (m.p. 190° C.) was obtained after recrystallization from ethanol-ether mixture.

EXAMPLE 8

(S)-1-o-Chlorophenyl-1,2-ethanediol (S)-1-o-Chlorophenyl-1,2-ethanediol (11.45 g, yield 92%, m.p. 39° C., $[\alpha]_D=74.7$ (c=2.75, methanol)) was prepared using the same synthetic method described in Example 4 except using hydroquinine 1,4-phthalazinediyl diether ((DHQ)$_2$PHAL) (562 mg) was used instead of quinidine.

EXAMPLE 9

(S)-2-Carbamoyloxy-1-o-chlorophenylethanol (S)-1-o-Chlorophenyl-1,2-ethanediol carbonate (12.58 g, yield 100%) was prepared using the same synthetic method described in Example 2 except that S-2-carbamoyloxy-1-o-chlorophenylethanol (10.98 g) was used instead of (D/L)-1-m-chlorophenyl- 1,2-ethanediol. The (S)-2-carbamoyloxy-1-o-chlorophenylethanol prepared in this manner was used in the synthetic method described in Example 6 for (D/L)-1-m-chlorophenyl-1,2-ethanediol carbonate to yield (S)-2-carbamoyloxy-1-o-chlorophenylethanol (4.68 g, yield 62%). An analytically pure sample of (S)-2-carbamoyloxy-1-o-chlorophenylethanol ethanediol (3.89 g, yield 52%, m.p. 133° C., $[\alpha]_D=64.9$ (c=2.69, methanol)) was obtained by recrystallization from ethyl acetate.

EXAMPLE 10

(R)-1-o-Chlorophenyl-1,2-ethanediol (S)-1-o-Chlorophenyl-1,2-ethanediol (11.45 g, yield 92%, m.p. 38° C., $[\alpha]_D=-64.5$ (c=3.5, methanol)) was prepared using the same synthetic method described in Example 4, except that hydroquinidine 1,4-phthalazinediyl diether ((DHQD)$_2$PHAL) (562 mg) was used instead of quinidine.

EXAMPLE 11

(R)-2-Carbamoyloxy-1-o-chlorophenylethanol (R)-1-o-Chlorophenyl-1,2-ethanediol carbonate was prepared using the same synthetic method described in Example 2, except that (S)-2-carbamoyloxy-1-o-chlorophenylethanol (10.98 g) was used instead of (D/L)-1-m-chlorophenyl-1,2-ethanediol. The crude (R)-2-carbamoyloxy-1-o-chlorophenylethanol prepared in this manner was used in the synthetic method described in Example 6 for (D/L)-1-m-chlorophenyl-1,2-ethanediol carbonate to yield (R)-2-carbamoyloxy-1-o-chlorophenylethanol (4.02 g, yield 54%). An analytically pure sample of (R)-2-carbamoyloxy-1-o-chlorophenylethanol ethanediol (3.35 g, yield 45%, m.p. 133° C., $[\alpha]_D$=−63.9 (c=2.22, methanol)) was obtained by recrystallization from ethyl acetate.

EXAMPLE 12

(S)-2-Carbamoyloxy-o-chlorophenylethyl carbamate (S)-2-Carbamoyloxy-o-chlorophenylethyl carbamate (1.6 g, yield 35%, m.p. 167°–169° C., $[\alpha]_D$=−84.1 (c=2.27, DMF)) was prepared using the same synthetic method described in Example 7, except that (S)-1-o-chlorophenyl-1,2-ethanol (3.0 g) was used instead of (D/L)-1-o-chlorophenyl-1,2-ethanediol.

EXAMPLE 13

(R)-2-Carbamoyloxy-o-chlorophenylethyl carbamate (R)-2-Carbamoyloxy-o-chlorophenylethyl carbamate (2.1 g, yield 46%, m.p. 172°–174° C., $[\alpha]_D$=84.9 (c=2.70, DMF)) was prepared using the same synthetic method described in Example 7, except that (R)-1-o-chlorophenyl-1,2-ethanol (3.0 g) was used instead of (D/L)-1-o-chlorophenyl-1,2-ethanediol.

The therapeutic use of the compounds of the present invention as anticonvulsants has been proven by the "Maximal ElectroShock (MES)" test, which is a well-established pharmacological screening method for anticonvulsants and the results are presented in Table I.

The procedure employed in the maximal electroshock test for anticonvulsants follows. The compound dosing solutions were prepared in saline, and the subjects, namely, mice (CF-1 strain), were dosed orally. After 1 hour, maximal electroshock were induced in mice via corneal electrodes using ITC Life Science model 11A Shocker at 50mA-60Hz for 0.2 second. Upon inducing maximal electroshock, the elimination of hindlimb tonic extension was considered as providing evidence of the protection by an anticonvulsant. The maximal electroshock test was performed at three different dose levels around the median efficacy dose (ED50) level of individual compound by using at least 8 mice in each group. ED50 value was calculated by the statistical method developed by Lichfield and Wilcoxon. Compounds with smaller ED50 value are more potent as anticonvulsant.

TABLE I

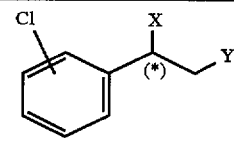

Oral administration in mice

| Compound of Example No | Position of Chlorine Atom | X with Stereochemistry (*) | Y | ED50 (mg/Kg) |
|---|---|---|---|---|
| 3 | m-Cl | (R/S)—OH | —OCONH$_2$ | 90 |
| 6 | o-Cl | (R/S)—OCONH$_2$ | —OH | 100 |
| 6 | o-Cl | (R/S)—OH | —OCONH$_2$ | 38 |
| 7 | o-Cl | (R/S)—OCONH$_2$ | —OCONH$_2$ | 25 |
| 9 | o-Cl | (R)—OH | —OCONH$_2$ | 13 |
| 11 | o-Cl | (S)—OH | —OCONH$_2$ | 50 |
| 12 | o-Cl | (S)—OCONH$_2$ | —OCONH$_2$ | 22 |
| 13 | o-Cl | (R)—OCONH$_2$ | —OCONH$_2$ | 16 |

It is to be understood that the present invention is not to be considered as limited to the embodiments shown or described, as obvious modifications and equivalents will be apparent to those skilled in the art.

What is claimed is:

1. An optically pure enantiomeric form excluding the racemic mixture of 2-carbamoyl-1-halophenylethanol compounds, represented by structural formula (I)

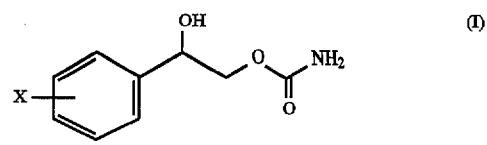

wherein X is chlorine and is substituted at the ortho position of the phenyl ring.

2. A pharmaceutical composition for treating disorders of the central nervous system consisting of as an active ingredient an effective amount for treating disorders of the central nervous system of a compound of Formula (I) as defined in claim 1 and a pharmaceutically acceptable carrier.

3. An optically pure enantiomeric form or an enantiomeric mixture, represented by structural formula (III)

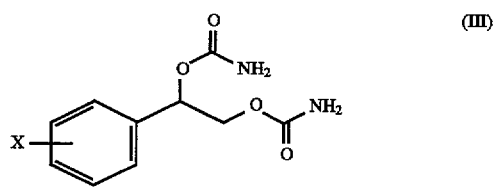

wherein X is a halogen atom substituted on the phenyl ring.

4. The compound of claim 3, wherein the halogen atom is selected from the group consisting of chlorine and fluorine.

5. The compound of claim 3, wherein the halogen atom is substituted at the ortho position of the phenyl ring.

6. The compound of claim 3, wherein the halogen atom is chlorine and is substituted at the ortho position of the phenyl ring.

7. A pharmaceutical composition for treating disorders of the central nervous system which comprises as an active ingredient an effective amount for treating disorders of the central nervous system of a compound of Formula (III) as defined in claim 3 and a pharmaceutically acceptable carrier.

* * * * *

UNITED STATES PATENT AND TRADEMARK OFFICE
CERTIFICATE OF CORRECTION

PATENT NO : 5,698,588

DATED : Dec. 16, 1997

INVENTOR(S): Choi, et al.

It is certified that error appears in the above-identified patent and that said Letters Patent is hereby corrected as shown below:

Column 1, lines 30-35, Formula II,

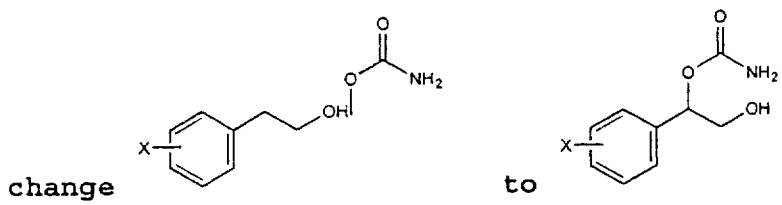

Column 3, lines 10-17, Formula II,

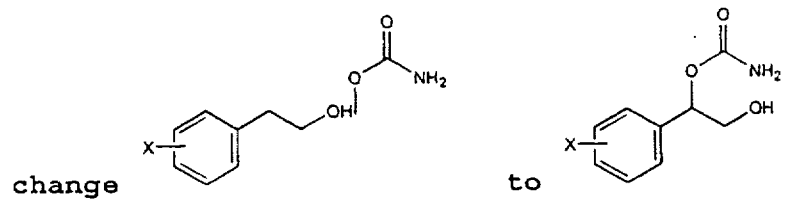

Column 3, line 39 change "dimethyl" to --diethyl--.

UNITED STATES PATENT AND TRADEMARK OFFICE
CERTIFICATE OF CORRECTION

PATENT NO : 5,698,588

DATED : Dec. 16, 1997

INVENTOR(S): Choi, et al.

Page 2 of 4

It is certified that error appears in the above-identified patent and that said Letters Patent is hereby corrected as shown below:

Column 4, lines 35-43, in Scheme 2, Formula III, change "$R_1$" and "$R_2$" to --H--;

Column 4, line 23, change "formulas (I) and (II)" to --formula III--

Column 5, line 22, change "1-phenyl" to --1-m-chlorophenyl--;

Column 5, line 65, change "D/L)-o-" to -- D/L)-1-o- --;

Column 6, line 43, delete "using";

Column 6, line 44, delete "instead of quinidine";

Column 6, lines 51 - 52, change "S-2-carbamoyloxy-1-o-chlorophenylethanol" to --(S)-1-o-chlorophenyl-1,2-ethanediol--;

Column 6, lines 53-54, change "(S)-2-carbamoyloxy-1-o-chlorophenylethanol" to --(S)-1-o-chlorophenyl-1,2-ethanediol carbonate--;

Column 6, line 56, change "-1-m-chlorophenyl-" to -- -1-o-chlorophenyl- --;

Column 6, line 58 change "chlorophenylethanoI" to --chlorophenylethanol--;

Column 6, line 60, delete "ethanediol".

UNITED STATES PATENT AND TRADEMARK OFFICE
CERTIFICATE OF CORRECTION

PATENT NO : 5,698,588
DATED : Dec. 16, 1997
INVENTOR(S): Choi, et al.

It is certified that error appears in the above-identified patent and that said Letters Patent is hereby corrected as shown below:

Column 6, line 66, change "(S)-1-o-Chlorophenyl-1,2-ethanediol" to --(R)-1-o-Chlorophenyl-1,2-ethanediol--

Column 7, line 3, delete "instead of quinidine";

Column 7, lines 11-12 change "(S)-2-carbamoyloxy-1-o-chlorophenylethanol" to --(R)-1-o-chlorophenyl-1,2-ethanediol--;

Column 7, lines 13-14 change "(R)-2-carbamoyloxy-1-o-chlorophenylethanol" to --(R)-1-o-chlorophenyl-1,2-ethanediol carbonate--;

Column 7 line 16 change "-1-m-chlorophenyl-" to -- -1-o-chlorophenyl- --;

Column 7, line 20, delete "ethanediol";

Column 7, lines 26-27, change "(S)-2-carbamoyloxy-o-chlorophenylethyl carbamate" to --(S)-2-carbamoyloxy-2-o-chlorophenylethyl carbamate--;

Column 7, lines 32-33, change "(S)-1-o-chlorophenyl-1,2-ethanol to -- (S)-1-o-chlorophenyl-1,2-ethanediol--;

Column 7, lines 36-37, change "(R)-2-carbamoyloxy-o-chlorophenylethyl carbamate" to --(R)-2-carbamoyloxy-2-o-chlorophenylethyl carbamate--;

UNITED STATES PATENT AND TRADEMARK OFFICE
CERTIFICATE OF CORRECTION

PATENT NO : 5,698,588
DATED : Dec. 16, 1997
INVENTOR(S): Choi, et al.

It is certified that error appears in the above-identified patent and that said Letters Patent is hereby corrected as shown below:

Column 7, line 43, change "(R)-1-o-chlorophenyl-1,2-ethanol to -- (R)-1-o-chlorophenyl-1,2-ethanediol--;

Column 8, Table 1, in the "X with Stereochemistry*" column, example No. 9, change "(R)-OH" to --(S)-OH--;

Column 8, Table 1, in the "X with Stereochemistry*" column, example No. 11, change "(S)-OH" to --(R)-OH--.

Signed and Sealed this

First Day of February, 2000

Attest:

*Attesting Officer*

Q. TODD DICKINSON

*Acting Commissioner of Patents and Trademarks*